United States Patent [19]

Olsen

[11] Patent Number: 4,581,763

[45] Date of Patent: Apr. 8, 1986

[54] CONTAINER FOR THE COLLECTION OF URINE AND/OR FAECES

[75] Inventor: Hans Olsen, Brønshøj, Denmark

[73] Assignee: Coloplast A/S, Denmark

[21] Appl. No.: 614,630

[22] Filed: May 29, 1984

[30] Foreign Application Priority Data

May 27, 1983 [DK] Denmark .............................. 2379-83

[51] Int. Cl.⁴ ......................... B65D 30/24; A61F 5/44
[52] U.S. Cl. ....................................... 383/49; 383/44;
383/57; 604/323; 604/335; 604/350
[58] Field of Search ..................... 383/904, 44, 48, 49,
383/57; 4/144.1, 144.2, 144.3; 604/317, 322,
323, 335, 349, 350; 128/760, 767, DIG. 24

[56] References Cited

U.S. PATENT DOCUMENTS

| | | | |
|---|---|---|---|
| 3,797,734 | 1/1974 | Fleury et al. | 383/44 |
| 3,823,716 | 7/1974 | Hale | 604/335 |
| 3,888,236 | 6/1975 | Marx | 128/767 |
| 4,421,509 | 12/1983 | Schneider et al. | 604/317 |
| 4,462,510 | 7/1984 | Steer et al. | 604/323 |

FOREIGN PATENT DOCUMENTS 135928 7/1974 Denmark .

Primary Examiner—John E. Kittle
Assistant Examiner—James J. Seidleck
Attorney, Agent, or Firm—Lawrence Rosen

[57] ABSTRACT

A container, which is flat in its empty condition, of plastic, rubber or another flexible material, especially for the collection of urine and/or faeces. The container comprises two outer walls (2) joined together in a surrounding seam (6), an inlet (54) and, if desired, an outlet (58). The inlet is provided with a non-return valve formed by enveloping a tube end (76) in two intermediate layers having the same extent as the outer walls (2) in the width direction of the container, the intermediate layers having free edges (80) spaced from the mouth (78) of the tube. The intermediate layers lie closely against each other in an area (56) situated between the edges (80) and the mouth (78) and delimited laterally by seams (72,74) joining the intermediate layers. In the length direction of the container the intermediate layers extend to a greater distance from the mouth (78) than the distance from the mouth (78) to the free edges (80), the free edges (80) bordering on an aperture (66) in each of the intermediate layers, which apertures (66) delimit the non-return valve. Preferably, the intermediate layers have the same extent as the two outer walls (2) both in the length and width directions and all four layers are joined together in the surrounding seam (6), preferably forming a flange (96) situated outside the seam (6). The outer walls (2) and the intermediate walls can be joined in longitudinal seams (8,10,12,14,16,18,20,22,24,26,28), running in the length direction of the container, forming a number of interconnected chambers, the intermediate walls being formed by the intermediate layers, which are joined with each other in a number of not through-going seams (24,26,28) and with the respective adjacent outer wall (2) in a number of not through-going secondary seams (8,10,12,14,16,18,20,22), said secondary seams being displaced with respect to said primary seams, and the intermediate layers have one or more apertures (66,68,86,88,90,92), preferably near the top and bottom of the container.

The container is suitable for large scale production. It has a reliable non-return valve, which eliminates the risk of leakages.

12 Claims, 2 Drawing Figures

CONTAINER FOR THE COLLECTION OF URINE AND/OR FAECES

THE FIELD OF THE INVENTION

The present invention relates to a container, which is essentially flat in its empty condition, of plastic, rubber or another flexible material, especially for the collection of urine and/or faeces, comprising two outer walls joined to each other by a surrounding seam, an inlet, and, if desired, an outlet, which inlet is provided with a non-return valve formed by enveloping a tube end in two intermediate layers, which layers have the same extent as the outer walls in the width direction of the container, and whereby the intermediate layers have free edges spaced from the mouth of the tube, which intermediate layers lie closely against each other in an area situated between the edges and the mouth and delimited laterally by seams joining the intermediate layers.

Such containers may for example be of the type in which the outer walls and the intermediate layers are joined with each other in longitudinal seams extending in the length direction of the container, forming a number of interconnected chambers.

Containers of the present kind are especially intended for the collection of faeces or urine, e.g. to be used by persons who have underwent an operation like colostomy, ileostomy or ureteromy, or especially for the collection of urine from incontinent patients.

BACKGROUND OF THE INVENTION

For obvious reasons it is an essential requirement that a container for the collection of urine or faeces is provided with a reliable non-return valve. Another important requirement of such containers is that they can be massproduced at a reasonable price.

It is known to use non-return valves formed by enveloping the end of the inlet tube in two foils, which are situated substantially in a plane comprising the central axis of the inlet tube end portion and which are delimited by the edges of the foils situated in a certain distance from the tube end, e.g. 2–3 cm. From the tube end the foils are joined in two diverging seams. Thereby the foils form a sort of extension of the inlet tube and do not impede the arriving liquid. When no liquid is arriving, the foils lie smoothly against each other preventing the liquid from returning, as a force would be needed for counteracting the adhesion forces between the two foils. This type of non-return valve, which in the present specification will also be termed "a foil valve", has the advantage of being mass-producable from simple materials.

In practice this foil valve has until now been manufactured in two different ways in connection with containers of the present kind. By the first method the valve and the container are produced within the same flow of work. In the inlet end of the container, the inlet tube is enveloped in two foil webs extending over the full width of the container. The edges of the foils are situated transversely to the longitudinal direction at a certain distance from the tube end. The foils are joined around the tube end and in the above-mentioned two diverging seams. Subsequently, the foils are covered with two further foils forming the outer walls of the container.

However, this construction involves the risk that the non-return valve may not be completely tight due to the occurance of windings and undulations in the valve foils when the container is filled and thereby bulging, the distance between the lateral seams of the container being shortened by the bulging, which means that the valve foils are pushed towards the central line. Under such conditions the foils will not be tight and flat, and the adhesion between the two foils will not be sufficient for preventing pockets, through which the content of the container can be forced back through the non-return valve.

It is known to avoid this by producing the foil valve separately around the tube end and by cutting away the superfluous foil material. This gives a foil valve lying freely inside the container. In this way, the valve foil will not be affected by lateral forces, e.g. when the container is bulging in filled condition, and windings or pockets do not occur in the valve and hence no leakages. Thereby, such a separately produced foil valve meets the functional requirements, but its production entails additional production costs, as first tubes provided with a valve at the tube end have to be produced, whereafter the resulting tubes can be used in the production of the container itself.

DK Patent Specification No. 135,928 discloses a container, which is flat in its empty condition, of plastic, rubber or another flexible material, which container comprises two outer walls joined to each other by a surrounding seam, and intermediate walls, said outer and intermediate walls being joined together in longitudinal seams extending in the length direction of the container and forming a number of interconnected chambers.

This known container is intended for being attached to the leg of the patient. In order to prevent splashing of the content of the container, thus avoiding embarrassing splash sounds, and in order to improve wearing comfort by reducing the forces of inertia from the liquid, i.e. to prevent movements of the liquid relative to the leg of the patient, the container is divided into mutually interconnected chambers. The container may for example consist of four layers of foil joined in seams, partly to seal the container and partly to delimit the chambers. In the known container the chambers are arranged in a row and are all bordering the outer walls, while the two intermediate foils partly form intermediate walls between the individual chambers and partly lie close to portions of the outer foils. Thus, the chambers are always limited to the outside by the two outer foils, but the outer foils are partially supplemented with one or both of the intermediate foils. This supplementing represents a waste of material, the outer foils having to be dimensioned in such a way that they by themselves are able to withstand the occurring load. In the areas having two or three layers of foils the intermediate layer or layers are not used for dividing the interior of the container into chambers, and in principle these layers could be omitted, but they have been included for productional reasons, as it is easier to produce a container, which is flat, i.e. essentially two-dimensional, in its empty condition, from four complete pieces of foil. Thus it is a drawback in the known container that the foil material included in the container is not utilized to an optimum for dividing the interior of the container into chambers, and thus a better utilization of the foil would be desirable in order to obtain more chambers by the division, each of the chambers becoming consequently smaller. The smaller the individual chambers the more the movements, if any, in the content of the container will be damped, i.e. the splashing tendency and the forces of inertia will be reduced.

SHORT DESCRIPTION OF THE INVENTION

It is an object of the invention to provide a container of the kind mentioned in the preamble, in which the non-return valve has the same reliability as the one obtained when the non-return valve is produced in a separate step by enveloping a tube end in two foils and cutting away the superfluous foil material, i.e. avoiding the drawbacks of leakage in connection with foil valves, which for productional reasons are produced by using foils having the same extent as the outer walls in the width direction of the container.

According to the invention this is obtained by letting the intermediate layers in the length direction of the container extend to a greater distance from the mouth than the distance from the mouth to the free edges, the free edges bordering on an aperture in each of the intermediate layers, which apertures delimit the non-return valve.

By providing the intermediate layers with apertures delimiting the non-return valve, the non-return valve will lie freely in the container in the same was as a separately produced foil valve, and the foil of the valve will not be pressed together in the lateral direction. In this way the likelihood of windings and pockets occurring in the foils of the valve is reduced and consequently the risk of leakages too. The same result would be obtained if the intermediate layers had been provided with incisions on both sides of the foil valve, but in that case the intermediate layers would not have uninterrupted edge areas. Foils with interruptions in the edge area are difficult to handle. The foils, which are usually supplied in band or web form, are difficult to control in the machines, because the foil web may tend to run slantwise in the machines due to the interruptions in the edge area, and the interruptions may easily lead to rupture of the webs. Thus, from a productional point of view it is important that the edge areas of the intermediate layers are uninterrupted. This is ensured by designing the container with the bottom edges of the intermediate layers being uninterrupted and situated at a distance from the free edges constituting a functional part of the non-return valve.

The apertures delimiting the non-return valve may advantageously be substantially U- or horseshoe-shaped, and it is further advantageous that the legs of the U- or horseshoe-shaped apertures have short distance to the delimiting seams, which seams converge towards the mouth of the tube lying tightly around the tube at the mouth, which legs extend substantially to the area surrounding the mouth. This ensures that the non-return valve is completely disengaged from the protions of the intermediate layers not forming part of the non-return valve. In this way the valve is protected optimally against lateral stresses, the risk of leakages being thereby avoided.

In order to ensure the proper functioning of the non-return valve with an adequate extent of the area, in which the foils of the valve lie closely against each other, the ratio of the distance between the mouth and the free edges to the distance between the seams at the free edges is to be between 1:1 and 3:1, preferably between 1.5:1 and 2:1.

In a particularly advantageous embodiment the intermediate layers have the same extent both in the length direction and in the width direction as the two outer walls and all four layers are jointed to each other in the surrounding seam, preferably forming a flange situated outside the seam. This ensures the same number of foil layers and thereby the same thickness of the material in the entire surrounding seam, in which the layers are joined. Usually the layers are joined by welding. In order to obtain a reliable and tight weld, it is important that the heating during the welding can be controlled, on one hand to ensure that the layers are joined without leaks, while on the other hand it is ensured that a heating so strong is prevented that the material becomes too soft or even melts away. The necessary and sufficient heating during the welding process depends upon the material thickness. Thus, it would be more difficult to produce a container without leaks if two foil layers are to be joined in some portions of the surrounding seam, whereas four foil layers are to be joined in other portions of the seam. Especially in the borders having a shift from two to four welded foil layers there is a risk of leakages. By the incorporation of the intermediate layers together with the outer walls in a flange situated outside the seam, a further stability of the container can be obtained. This flange is also a suitable place for supporting means, e.g. in case of a container for collection to be carried by a patient, e.g. secured to the leg of the patient.

The principle of the above-mentioned specific embodiment, in which the intermediate layers have the same extent as the outer walls both in the length and width directions, may be particularly advantageous to use in connection with the known type of container, which must have intermediate walls in addition to the outer walls, whereby the outer walls and the intermediate walls are joined to each other in longitudinal seams running in the length direction of the container and forming a number of interconnected chambers. In this case the intermediate walls may advantageously be formed by the intermediate layers, which are joined with each other in a number of not through-going primary seams and with the respective adjacent outer wall in a number of not through-going secondary seams, said secondary seams being displaced with respect to said primary seams, and the intermediate layers having one or more apertures, preferably near the top or the bottom of the container.

Besides the essential advantages obtained in this way with respect to production technique and utilization of the material used, i.e. by utilizing the intermediate layers both for the construction of the non-return valve, for the reinforcement of the surrounding flange, and as intermediate walls for the division into interconnected chambers, the embodiment described above offers the further advantage over the container disclosed in DK Patent Specification No. 135,928 that the intermediate layers are better utilized for the division into chambers. Thus, by using the same number of foil layers, a division into a greater number of chambers is achieved, each chamber being consequently smaller, e.g. 10 chambers compared to a divison into only 5 chambers obtained according to an embodiment disclosed in the DK patent specification mentioned above, in which case the number of joints is of the same order of magnitude. This improved utilization of the foil material results from the mutual arrangement of the primary and secondary seams, in accordance with which care is taken that two or three foils do not to a considerable extent lie closely against each other without utilization of an interspace between them as a chamber in the container.

In two further embodiments of the invention the container is also provided with a number of interconnected chambers formed by intermediate walls joined in longitudinal seams. According to the first one of these two embodiments the intermediate walls are formed by two wall layers having the same extent as the outer walls in the width direction and extending from a level below the downward edge of the intermediate layers to the downward end of the container in the length direction, said wall layers being joined with each other in a number of not through-going primary seams and with the respective adjacent outer wall in a number of not through-going secondary seams, said secondary seams being displaced with respect to said primary seams, and the wall layers having one or more apertures near the bottom of the container. In this embodiment the further apertures can be omitted in the top part of the container, i.e. only the aperture delimiting the non-return valve must be present in the top part.

In the second one of these two embodiments the intermediate walls are formed by two wall layers having the same extent as the outer walls in the width direction and extending from a level below the downward edge of the intermediate layers to a level at a short distance above the surrounding seam in the bottom end of the container in the length direction, said wall layers being joined with each other in a number of not through-going primary seams and with the respective adjacent outer wall in a number of not through-going secondary seams, said secondary seams being displaced with respect to said primary seams. In this embodiment also the apertures near the bottom of the container can be omitted. Also the last-mentioned two embodiments give a better utilization of the foil layers for division into chambers as compared with the division arrangement proposed in DK Patent Specification No. 135.928.

DETAILED DESCRIPTION OF THE INVENTION

Figure 1:
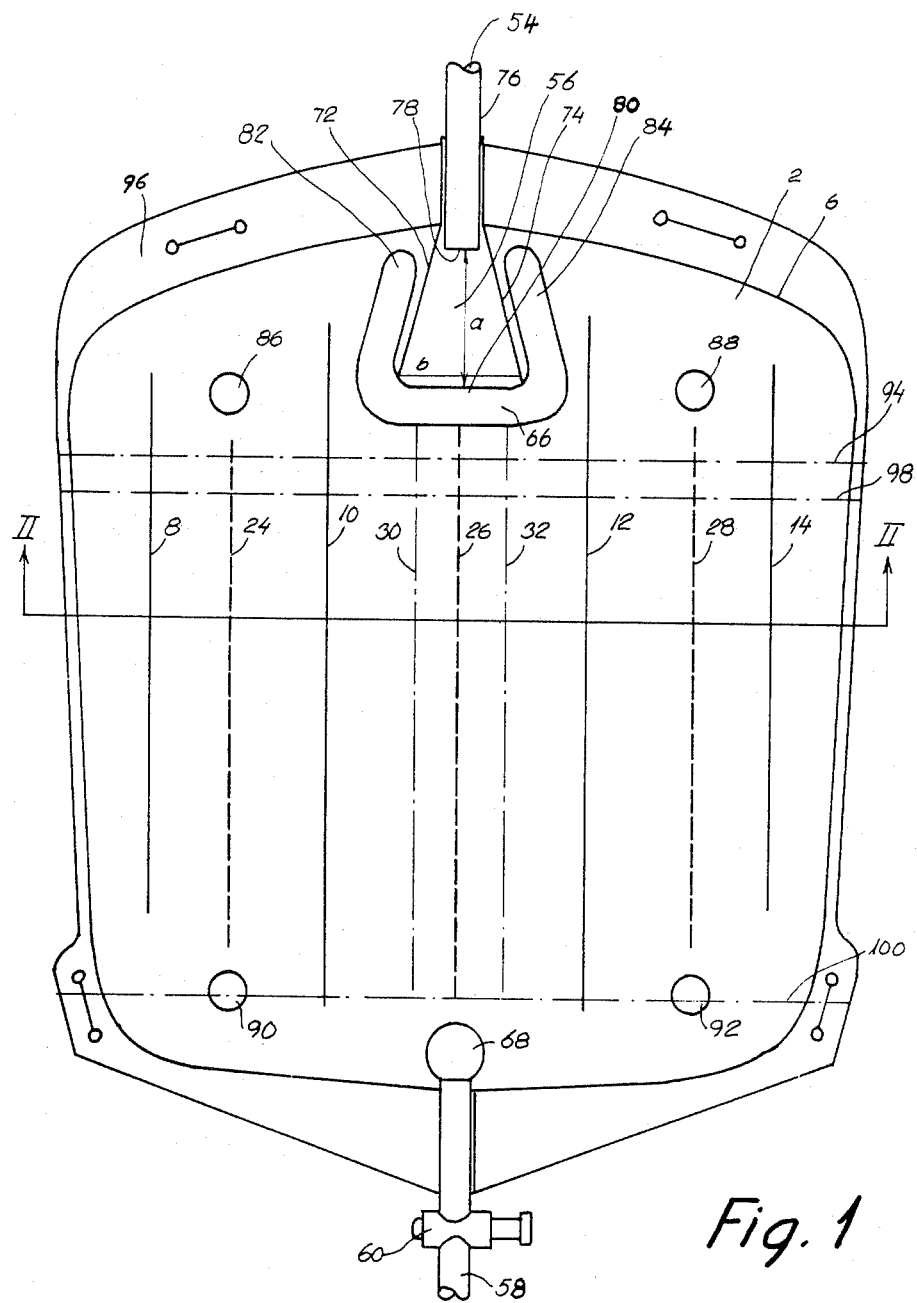

The invention will now be described in detail with reference to an embodiment illustrated in the drawing. In the drawing FIG. 1 is a schematic illustration of a container according to the invention in its empty and consequently flat condition, and FIG. 2 is a cross-section taken along the line II—II through the container of FIG. 1 in the filled and consequently bulging condition.

Figure 2:
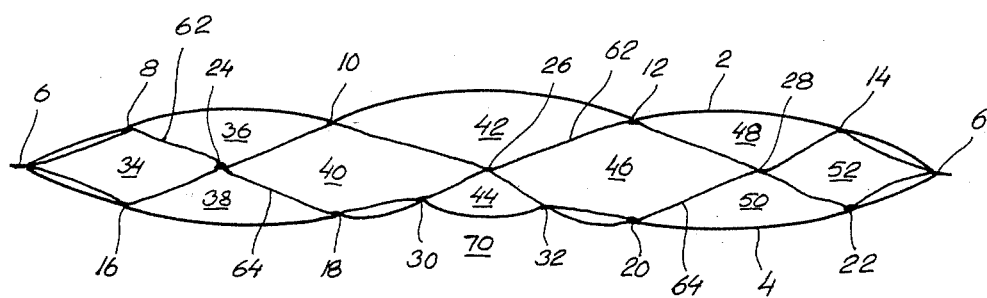

The container illustrated in FIGS. 1 and 2 comprises four foils forming two outer walls 2,4 and two intermediate layers 62,64, which foils are joined to form a closed container by using an adhesive, welding or another joining in a surrounding seam 6. The container has an inlet 54 with a valve of the type termed a foil valve in the present specification, and an outlet 58 with an outlet valve 60. In a non-illustrated embodiment of the invention the outlet 58 and the outlet valve 60 may be omitted, whereby the joint seam 6 will be continuous in the bottom part of the container.

The foil valve is made by enveloping the end of the inlet 54, which is in the present case formed by a tube end 76 between the foils constituting the intermediate layers 62,64. In an area 56 the foil valve comprises two foil layers lying closely against each other but only held together by the mutual adhesion between the two foils. This area is laterally delimited by two joint seams 72,74 joining the two foils, e.g. formed by welding; downwardly the area is delimited by the concurrent free edges 80 forming the opening of the valve leading into the interior of the container. Upwards the area 56 is delimited by the mouth 78 of the tube end 76. The welding seams 72,74 extend right up to the surrounding seam 6, which is close to the tube 76. Thus the area 56 is only open through the mouth 78 and between the free edges 80. The function of the foil valve is that a liquid can easily flow through the mouth 78 of the tube 76 and into the area 56, in which the two foils are pressed from each other by the liquid which then flows into the container between the two free edges 80. When no liquid flows from the tube 76 into the container, the two foils will lie closely against each other in the area 56 with a mutual adhesion sufficient to prevent the liquid from being forced from the container into the area 56 between the foils, but not sufficient to give a perceptible resistance to liquid flowing from the mouth 78 into the area.

In the width direction the intermediate layers 62,64 have the same extent as the two outer walls 2,4. In the embodiment shown they also have the same extent as the outer walls in the length direction. However, it is sufficient that in the length direction they extend to a distance from the mouth 78, which is greater than the distance (a) from the mouth 78 to the free edges 80. In other words, it is not the downward edges of the intermediate layers 62,64, which are to function as an opening in the foil valve in the form of the free edges 80. On the contrary, these free edges are attained by providing the intermediate layers with an aperture 66. This aperture 66 can delimit the foil valve, e.g. by giving the aperture horseshoe-shape or U-shape, the result being that the foil valve is cut free from the surrounding foil, which means that it is not affected by lateral forces when the container is filled with liquid and bulges. If the downward extent of the intermediate layers were concurrent with the free edges 80 and the valve were cut free by incisions made at the legs 82,84 of the U-shaped aperture 66 in the shown embodiment, a valve not being affected by lateral forces would be obtained in the same way. However, such a design would cause difficulties in production, as problems would arise if the intermediate layers 62,64 were supplied in the form of rolled up foil webs having interruptions in the form of incisions in one of the side edges, whereby the foil webs would tend to run askew or aslant or even to crack or tear. If, on the other hand, the intermediate layers extend at least some distance beyond the aperture 66, e.g. with the downward edge situated as shown with a dot-and-dash line 94 in FIG. 1, there will be an uninterrupted edge along the line 94, whereby the guiding and controlling of the foil webs to be used for forming the intermediate layers 62,64 will be facilitated.

In the embodiment shown the intermediate layers have the same extent also in the length direction as the outer walls 2,4. This ensures that the same number of foil layers will be joined throughout the whole of the surrounding seam 6. This is advantageous in case of joining by welding, the controlling of the welding being facilitated. If some areas have only two layers of foil and some other areas four layers, a particular risk of leakages in the weld seam 6 would exist at the shifts from two to four layers of foil. Outside the surrounding seam 6 the outer wall 2,4 and the intermediate layers 62,64 together form a flange 96, which stiffens the container. The flange 96 may be further stiffened, e.g. with an additional surrounding seam (not shown). This flange may suitably be used for the mounting of support means (not shown) for supporting the container, e.g. in such a way that it can be worn by a patient.

In the embodiment shown in the drawing the intermediate layers 62,64 are further used for dividing the container into interconnected chambers 34,36,38,40,42,44,46,48,50,52. This division is made by joining the two intermediate layers 62,64 by an adhesive, by welding or by using any other joining technique, in seams 24,26,28. The top foil layer, i.e. the outer wall 2 (FIG. 2) is joined with the adjacent intermediate layer 62 by use of an adhesive, by welding or by any other per se known means, in seams 8,10,12,14, and similarly the bottom foil layer, i.e. the outer wall 4, is joined with the adjacent intermediate layer 64 in seams 16,18,20,22. As shown in FIG. 2 all of the layers are joined in the surrounding seam 6 too. Two additional joints 30,32 are provided on the back of the container giving the container a cross-section with a recess 70. This recess facilitates the securing of the container to the leg of the user.

As the intermediate layers 62,64 extend further upwards and downwards than the surrounding seam, it is necessary that the intermediate layers are provided with apertures 66,86,88 near the top of the container and with further apertures 68,90,92 near the bottom of the container and close to the outlet 58. This ensures that the chambers are mutually connected. It is also possible in case the intermediate layers do not have the same extent as the outer walls 2,4 in the length direction to utilize the intermediate layers for the division into chambers if the downward edge of the intermediate layers is situated at a short distance from the lower part of the container, i.e. at a short distance from the surrounding seam 6 in the area around the outlet 58 of the container, e.g. as shown with a dot-and-dash line 100 in FIG. 1. In that case, the apertures 68,90,92 near the bottom of the container can be omitted.

In case the downward edges 94 of the intermediate layers only have a short distance from the free edges 80 of the foil valve, e.g. as shown by the dot-and-dash line 94 in FIG. 1, the container may be provided with additional foils in the form of two wall layers having the same extent as the outer walls in the width direction and extending from a level shown with a dot-and-dash line 98 in FIG. 1, below the downward edge 94 of the intermediate layers to a level near the bottom of the container. In that case the wall layers can form the intermediate walls if the wall layers are joined with each other in a number of not through-going primary seams and with the respective adjacent outer walls 2,4 in a number of secondary seams, said secondary seams being displaced with respect to said primary seams. This will give the same division into chambers as in the embodiment shown in FIGS. 1 and 2. The primary and secondary seams can be situated as shown in FIG. 1, but of course only extending within the wall layers. The space between the intermediate layers and the wall layers means that the apertures 86,88 shown in FIG. 1 can be omitted. The downward edge of the wall layers may either extend beyound the seam 6 in the bottom part of the container, in which case the wall layers form a portion of the flange 96 and they should be provided with apertures 68,90,92 near the bottom of the container, or the downward edge of the wall layers may end at a short distance above the surrounding seam 6 in the bottom end of the container, e.g. as shown with the line 100 in FIG. 1, in which case the apertures 68,90,92 may be omitted.

The container according to the invention may for example be made of a thermoplastic material, which can be joined by welding. An example of such a thermoplastic material is PVC-foil. However, the container can also be made of rubber or another flexible material, e.g. using an adhesive for the joining.

INDUSTRIAL USE OF THE INVENTION

The invention is expected to have the greatest impact within industries producing incontinence bags, stoma bags, and similar articles.

The invention is also expected to become of importance within other industries wanting to manufacture low-priced containers having a reliable non-return valve on an industrial scale.

I claim:

1. A container, which is essentially flat in its empty condition, of plastic, rubber or another flexible material, comprising two outer walls joined to each other by a surrounding seam, an inlet generally aligned with a length direction of the container, which inlet is provided with a non-return valve formed by enveloping a tube end in two intermediate layers, which layers have the same extent as the outer walls in the width direction of the container, and wherein the intermediate layers have free edges spaced from the mouth of the tube, which intermediate layers lie closely against each other in an area situated between the free edges and the mouth and delimited laterally by seams joining the intermediate layers, and wherein the intermediate layers in the length direction of the container extend to a greater distance from the mouth than the distance from the mouth to the free edges, the free edges bordering on an aperture in each of the intermediate layers, which apertures delimit the non-return valve.

2. A container according to claim 1, wherein the apertures are substantially U-shaped or horseshoe-shaped.

3. A container according to claim 2, wherein the legs of the U- or horseshoe-shaped apertures are closely spaced to the delimiting seams, said seams converge towards the mouth of the tube lying tightly around the tube at the mouth, and the legs extend substantially to the area surrounding the mouth.

4. A container according to claim 2, wherein the ratio of the distance between the mouth and the free edges to the distance between the seams at the free edges is between 1:1 and 3:1.

5. A container according to claims 1, 2, 3 or 4 wherein the intermediate layers both in the length and the width directions have the same extent as the outer walls and wherein all four of these layers are joined to each other in the surrounding seam, preferably forming a flange situated outside the seam.

6. A container according to claim 5, having intermediate walls, wherein the outer walls and the intermediate walls are joined to each other in longitudinal seams, which run in the length direction of the container and form a number of interconnected chambers, and wherein the intermediate walls are formed by the intermediate layers, which are joined with each other in a number of primary seams respectively connecting only said two intermediate walls and with the respective adjacent outer wall in a number of secondary seams respectively connecting only a respective outer wall to a respective intermediate wall, said secondary seams being displaced with respect to said primary seams, and wherein the intermediate layers have one or more apertures.

7. A container according to any one of claims 1–4, having intermediate walls, wherein the outer walls and the intermediate walls are joined with each other in longitudinal seams running in the length direction of the container and forming a number of interconnected chambers, and wherein the intermediate walls are formed by two wall layers having the same extent as the outer walls in the width direction and extending from a level below the downward edge of the intermediate layers to the downward end of the container in the length direction, said wall layers being joined with each other in a number of primary seams repectively connecting only said two intermedite walls and with the respective adjacent outer wall in a number of secondary seams respectively connecting only a respective outer wall to a respective intermediate wall, said secondary seams being displaced with respect to said primary seams, and wherein the wall layers have one or more apertures near the bottom of the container.

8. A container according to any one of claims 1–4, having intermediate walls, wherein the outer walls and the intermediate walls are joined with each other in longitudinal seams running in the length direction of the container and forming a number of interconnected chambers, and wherein the intermediate walls are formed by two wall layers having the same extent as the outer walls in the width direction and extending from a level below the downward edge of the intermediate layers to a level at a short distance above the surrounding seam in the bottom end of the container in the length direction, said wall layers being joined with each other in a number of primary seams respectively connecting only said two intermediate walls and with the respective adjacent outer wall in a number of secondary seams respectively connecting only a respective outer wall to a respective intermediate wall, said secondary seams being displaced with respect to said primary seams.

9. A container according to claim 1, having an outlet.

10. A container according to claim 4, wherein the ratio of the distance between the mouth and the free edges to the distance between the seams at the free edges is between 1.5:1 and 2:1.

11. A container according to claim 5, wherein all four layers are joined to each other in the surrounding seam and form a flange situated outside the seam.

12. A container according to claim 6, wherein the apertures in the intermediate layers are located near the top and the bottom of the container.

* * * * *